US006886210B2

(12) United States Patent
Dean

(10) Patent No.: US 6,886,210 B2
(45) Date of Patent: May 3, 2005

(54) ANTI-MICROBIAL FLOOR MAT

(75) Inventor: Michael T. Dean, Saratoga Springs, NY (US)

(73) Assignee: Saratoga Hotel Group, LLC, Saratoga Springs, NY (US)

( * ) Notice: Subject to any disclaimer, the term of this patent is extended or adjusted under 35 U.S.C. 154(b) by 202 days.

(21) Appl. No.: 10/214,394

(22) Filed: Aug. 7, 2002

(65) Prior Publication Data

US 2003/0029477 A1 Feb. 13, 2003

Related U.S. Application Data

(60) Provisional application No. 60/311,001, filed on Aug. 8, 2001.

(51) Int. Cl.[7] .............................................. A47L 23/26
(52) U.S. Cl. ........................ 15/215; 15/104.92; 15/216
(58) Field of Search .......................... 15/215, 216, 217, 15/104.92

(56) References Cited

U.S. PATENT DOCUMENTS

| | | | | |
|---|---|---|---|---|
| 3,578,738 A | * | 5/1971 | Hughes ........................ | 15/215 |
| 3,696,459 A | | 10/1972 | Kucera et al. | |
| 4,425,677 A | | 1/1984 | Cox | |
| 4,800,677 A | * | 1/1989 | Mack ........................... | 119/171 |
| 4,822,669 A | * | 4/1989 | Roga ........................... | 442/373 |
| 5,071,628 A | | 12/1991 | Alazet | |
| 5,297,309 A | | 3/1994 | Rotoli | |
| 5,792,712 A | | 8/1998 | Hori et al. | |
| 6,146,588 A | | 11/2000 | Deighton | |
| 6,219,876 B1 | | 4/2001 | Blum | |
| 6,233,776 B1 | | 5/2001 | Blum et al. | |
| 6,258,435 B1 | | 7/2001 | Staal | |
| 6,463,885 B1 | * | 10/2002 | Laner ......................... | 119/652 |

* cited by examiner

*Primary Examiner*—Randall Chin
(74) *Attorney, Agent, or Firm*—Michael Best & Friedrich LLP

(57) ABSTRACT

A floor mat system for placement directly near an entryway to permit the disinfecting and cleaning of shoe soles and all other surfaces contacting directly with the fibers of the mat. The floor mat system consists of a frame structure either mechanical or rubberized in construction. The top portion being of a carpet type fiber construction, with a hollow center portion and rubberized non-skid backing against the floor and sides. The hollow center portion of the system may be enclosed and a microbicidal component introduced to the carpet fiber portion in a capillary action. Alternatively, the microbicidal component may be contained in a separate enclosed package which is introduced to the carpet fiber portion through spray heads located on the enclosed package in a pressure action activated by weight on the top carpet layer. The floor mat system may also be integrated into other floor or carpet. The floor mat system may also include a moisture absorbing component, a cushioning component, customized graphics, anti-fungal composition, or a fragrance. Anti-slip features may be associated with the mat to prevent slipping. Additionally, a sensor may be included in the floor mat to assist a user in identifying when the floor mat system may require refill of the microbicidal component.

22 Claims, 6 Drawing Sheets

ANTI-MICROBIAL FLOOR MAT

This application claims the benefit of prior filed co-pending provisional patent application No. 60/311,001 filed on Aug. 8, 2001.

FIELD OF THE INVENTION

The invention relates to cleaning, and more particularly to the disinfecting of ground contacting surfaces such as feet, shoe soles, wheels, and the like.

BACKGROUND OF THE INVENTION

Floor mats have long been used to clean the soles of a person's feet or shoes before entering a building or room. Typically these mats are placed on the ground in front of doors and entryways. These mats are often made of abrasive materials to promote the removal of debris when someone wipes his or her feet across the surface of the mat.

SUMMARY OF THE INVENTION

The present invention provides a floor mat system for placement near an entryway to permit the disinfecting and cleaning of shoe soles and all other surfaces contacting directly with the fibers of the mat. The floor mat system includes a frame having a top portion being of a carpet type fiber construction, a hollow center portion, a floor portion, and sidewalls. The hollow center portion contains a microbicidal component such that the component may be communicated to the top portion of the mat.

The hollow center portion of the system may be completely enclosed and a microbicidal component may be introduced to the carpet fiber portion by capillary action. Alternatively, a separate enclosed package containing the microbicidal component may be used such that the liquid is introduced to the carpet fiber portion in a pressure action through spray heads that may be activated by weight on the top carpet layer. The floor mat system may also be integrated into other floor or carpet. The floor mat system may also include a moisture absorbing component, a cushioning component, customized graphics, anti-fungal composition, or a fragrance. Anti-slip features may be associated with the top surface of the mat to prevent a person or animal from slipping on the mat. Anti-slip features may also be associated with the bottom and side surfaces of the mat to prevent the mat itself from slipping along the floor or ground. Additionally, a sensor may be included in the floor mat to indicate that the floor mat system may require refill of the microbicidal component Other features and advantages of the invention will become apparent to those skilled in the art upon review of the following detailed description, claims, and drawings.

Figure 1:
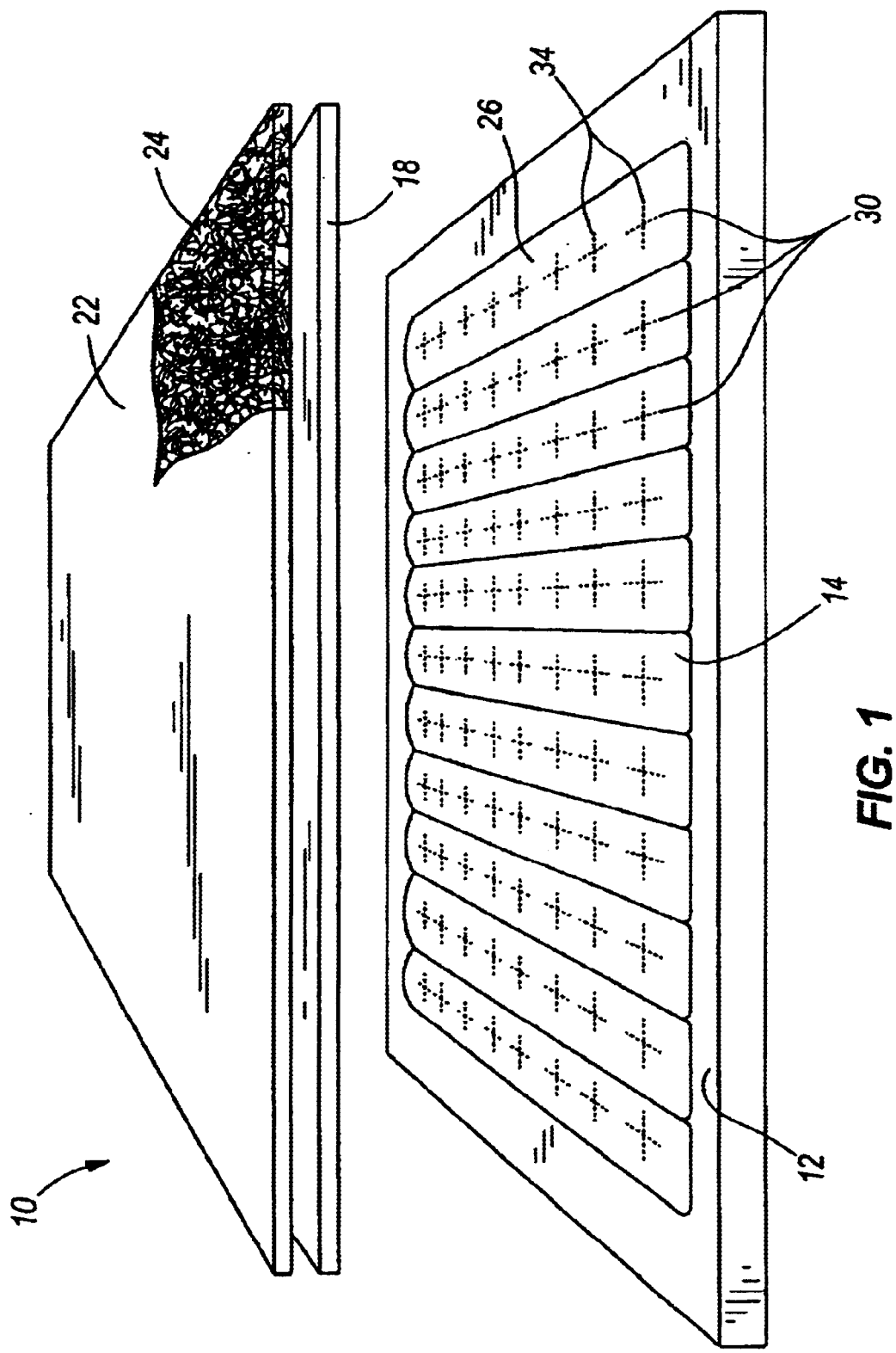
FIG. 1 shows a first embodiment of the anti-microbial mat of the present invention.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION OF THE PREFERRED EMBODIMENT

FIG. 1 shows an anti-microbial floor mat 10 of the present invention. The mat 10 includes a frame 12, a membrane 14 configured to contain a cleaning solutions such as, for example, an anti-microbial liquid, a mesh backing 18, and an absorbent carpet fiber portion 22. The frame 12 is configured to support the membrane 14 such that the membrane 14 generally conforms to the shape of the frame 12. The frame 12 may be of any suitable construction that will rigidly support the membrane 14 and other components of the mat 10. The membrane 14 includes an upper surface 26 having a plurality of sprayheads 30 defined therein. The sprayheads 30 are characterized by a plurality of holes 34 in the upper surface 26 of the membrane 14. The sprayheads 30 may be arranged into rows and columns extending between the edges of the upper surface 26 or may be randomly spaced along the upper surface 26. The mesh backing 18 is coupled to the upper surface 26 of the membrane 14 and provides a fluid permeable layer between the sprayheads 30 and the carpet fiber portion 22. The carpet fiber portion 22 includes a plurality of individual carpet fibers 24 coupled to the mesh backing 18. Both the mesh backing 18 and the carpet fiber portion 22 extend across substantially the entire length and width of the frame 12 to cover the membrane 14 and form a single, continuous mat 10.

When an object (e.g. the foot of a person or animal) is placed onto the anti-microbial mat 10 including the membrane 14 filled with anti-microbial fluid, the weight of the object on the mat 10 causes the internal pressure in the membrane 14 to increase. The increase in pressure causes the anti-microbial liquid to be expelled from the membrane 14 through the sprayheads 30 in the upper surface 16. The liquid flows through the mesh backing 18 and is absorbed by the carpet fiber portion 22. The liquid is absorbed by the fibers 24 of the carpet fiber portion 22 and the upper surface of the carpet fiber portion 22 becomes moist with anti-microbial liquid. As the object moves across the anti-microbial mat 10, anti-microbial liquid is transferred from the fibers 24 of the carpet fiber portion 22 to surfaces of the object that contact the mat 10.

Figure 2:
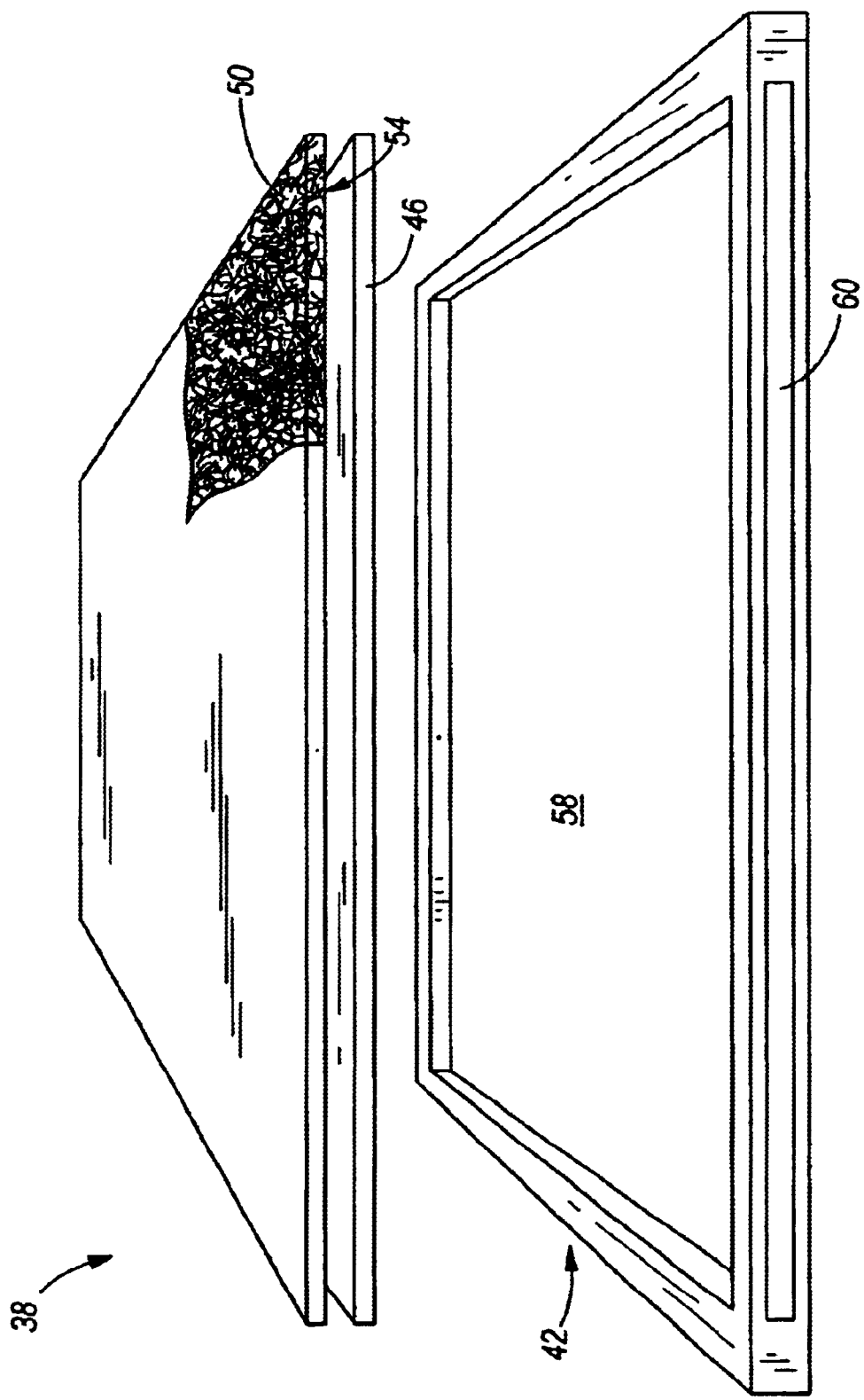
FIG. 2 is an exploded view of a second embodiment of the anti-microbial mat of the present invention.
Figure 3:
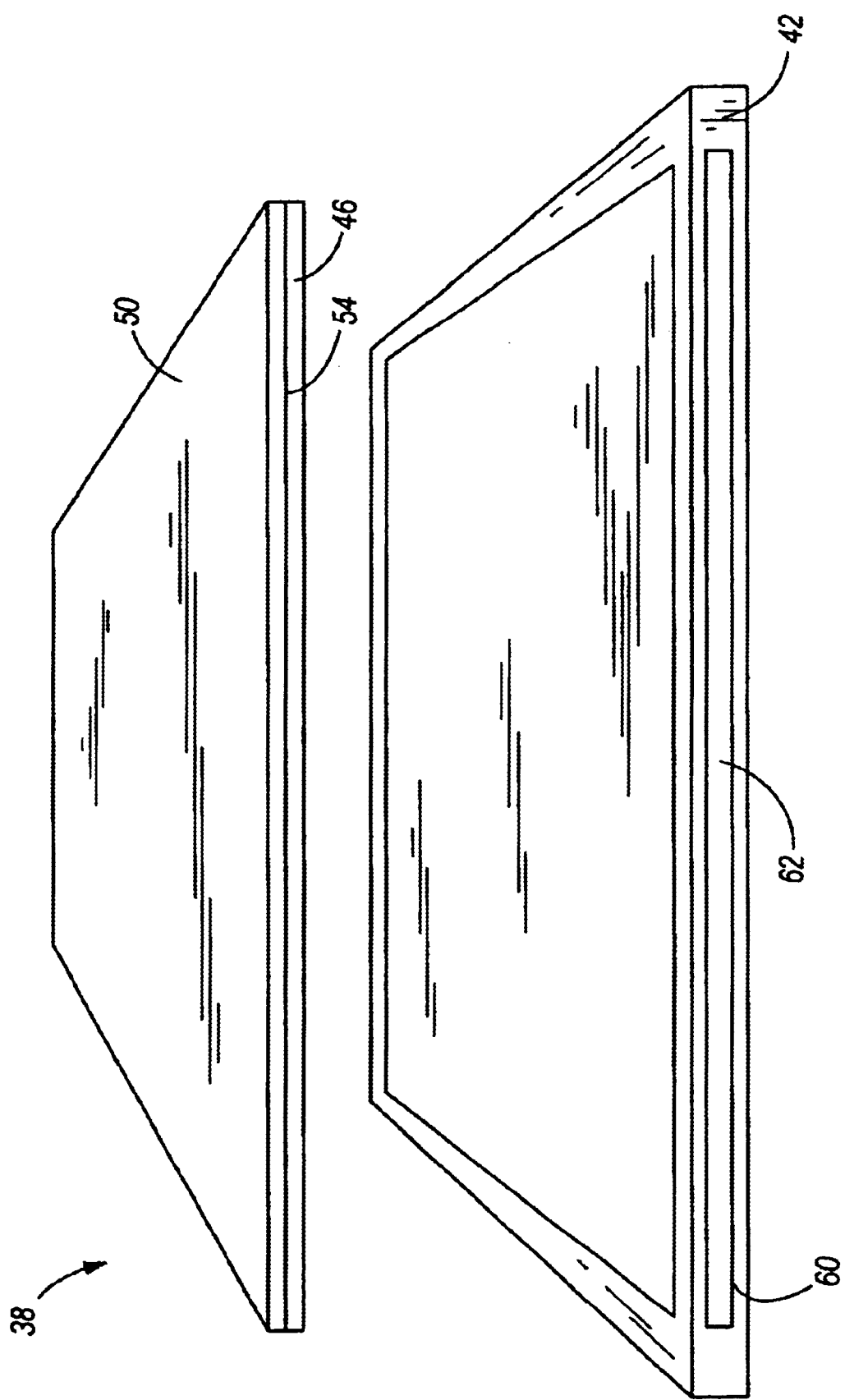
FIG. 3 is a partially exploded view of the anti-microbial mat shown in FIG. 2.
Figure 4:
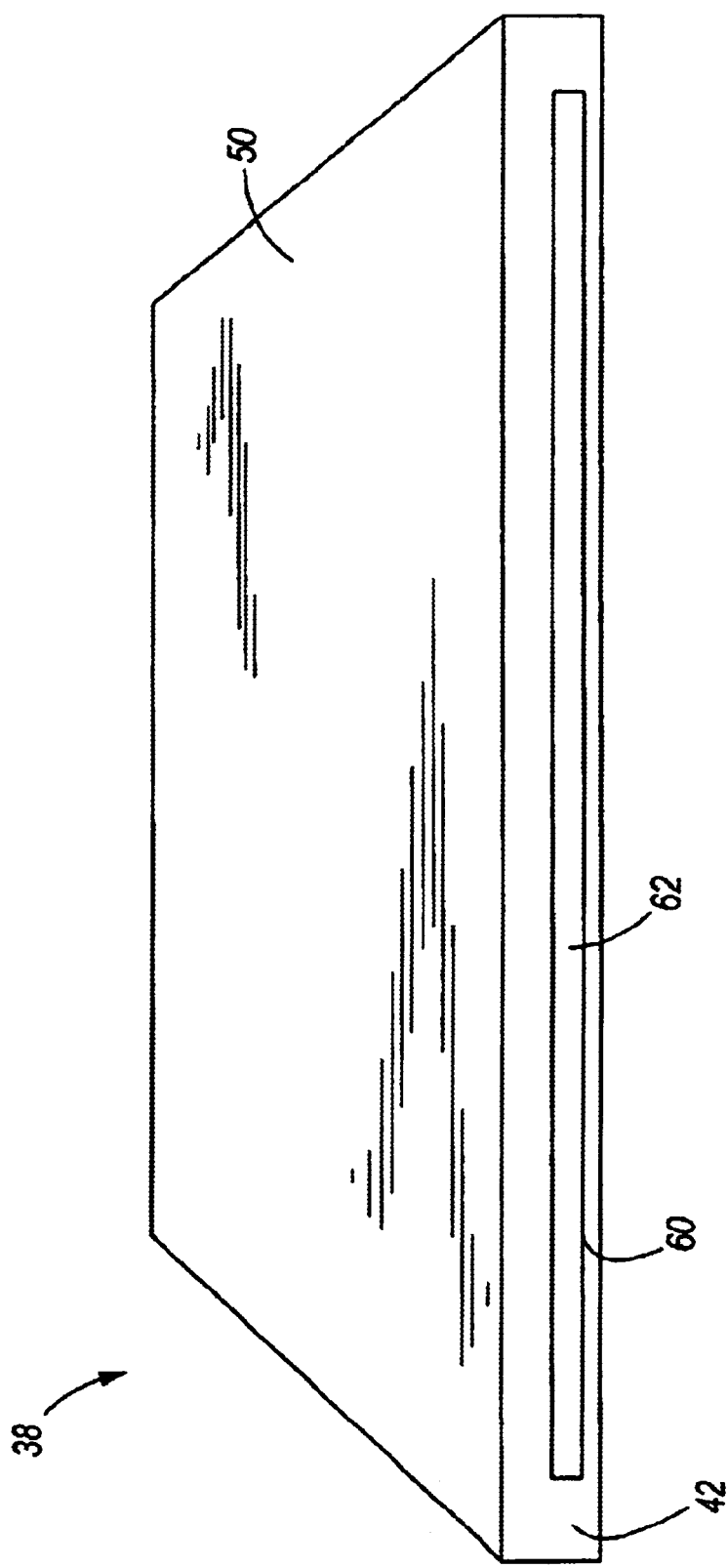
FIG. 4 is an assembled view of the anti-microbial mat shown in FIG. 2.

Referring now also to FIGS. 2–4, another embodiment of the present invention is shown. The mat 38 includes a substantially rigid frame 42, a sprayhead layer 46, and a carpet fiber portion 50 including an integral mesh backing 54. The base 42 includes a recessed area 58 configured to receive a disposable anti-microbial liquid-containing cartridge 62 (not shown in FIG. 2). The base 42 may also include a cartridge opening 60 defined in a side of the base 42 to facilitate the insertion and removal of the cartridge 62. The sprayhead layer 46 includes a plurality of sprayheads 64 (not shown but similar to sprayheads 30) configured to puncture the cartridge 62 and provide fluid communication between the cartridge 62 and the carpet fiber portion 50. The carpet fiber portion 50 and mesh backing 54 are of similar construction as the portion 22 and backing 18.

When an object (e.g. the foot of a person or animal) is placed onto the anti-microbial mat 38, the weight of the object forces the sprayhead layer 46 against the cartridge 62, thereby puncturing the cartridge. The weight of the object also increases the internal pressure in the cartridge 62 such that the anti-microbial liquid is expelled from the cartridge 62. The liquid flows through the sprayhead layer 46 and mesh backing 54 and is absorbed by the carpet fiber portion 50. The liquid is absorbed by the fibers of the carpet fiber portion 50 and the upper surface of the carpet fiber portion 50 becomes moist with anti-microbial liquid. As the object moves across the anti-microbial mat 10, anti-microbial liquid is transferred from the fibers to surfaces of the object that contact the mat 10. When all of the anti-microbial liquid has been expelled from the cartridge 62, the spent cartridge 62 is removed from the base 42 and discarded. A new cartridge 62 is then inserted into the recessed area 58 of the base. In alternative embodiments, the cartridge 62 may take on the form of an anti-microbial liquid containing tray. In this form, the sprayhead layer 46 construction may be simplified due to the fact that it is no longer necessary to puncture the cartridge 62.

Figure 5:
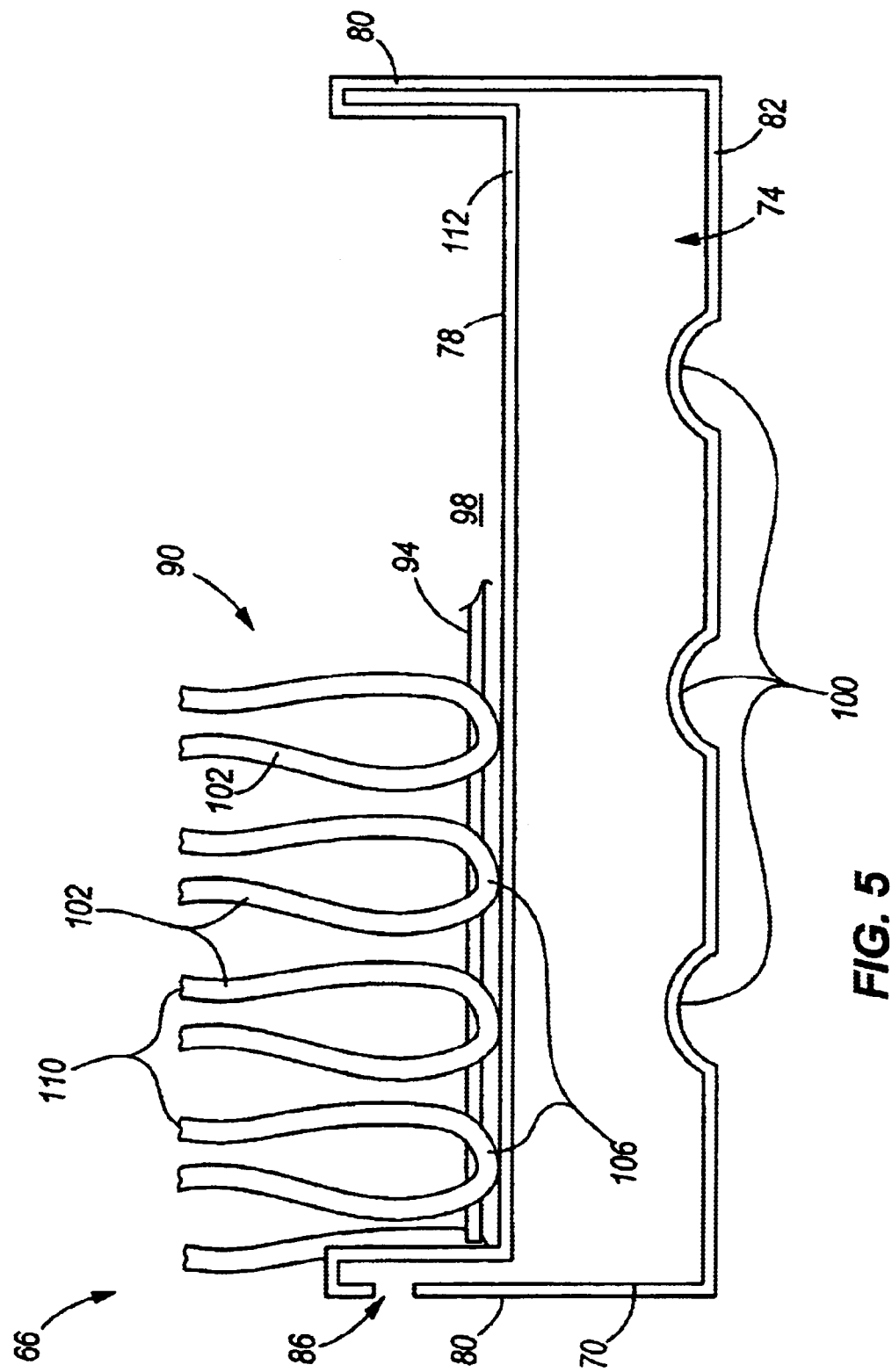
FIG. 5 is a sectional view of a third embodiment of the anti-microbial mat of the present invention.

FIG. 5 shows another embodiment of the present invention wherein the mat 66 takes on a "one-piece" construction and includes a substantially rigid base 70 that defines an anti-microbial liquid containing chamber 74. The base 70 includes an upper wall 78, sidewalls 80, and a lower wall 82. One sidewall 80 includes an aperture 86 defined therein communicating with the chamber 74. The aperture 86 is configured to allow anti-microbial liquid to be injected or otherwise introduced into the chamber 74 as required while maintaining a substantially fluid tight seal when liquid is not being introduced into the chamber 74. A carpet fiber portion 90 including an integral mesh backing 94 are placed in a recess 98 defined in the upper wall 78. The lower wall 82 may include a plurality of ribs 100 to structurally stiffen the base 70.

The carpet fiber portion 90 includes a plurality of carpet fibers 102. The carpet fibers 102 are arranged into a U-shape and include a fixed end 106 and a free end 110. The fixed end 110 is generally fixed to the mesh backing 94. The upper wall 78 includes a fluid conducting layer 112 that allows fluid to pass from the chamber 74 to the recess 98 where it may be absorbed by the carpet fiber portion 90 and conveyed to the free ends 110 of the carpet fibers by capillary action. The recess 98 and upper wall are 78 are configured such that the fixed ends 106 of the carpet fibers 102 are submerged in fluid when the chamber 74 is full. As such, the free ends 110 of the carpet fiber portion 90 are substantially continuously moist with anti-microbial fluid.

Figure 6:
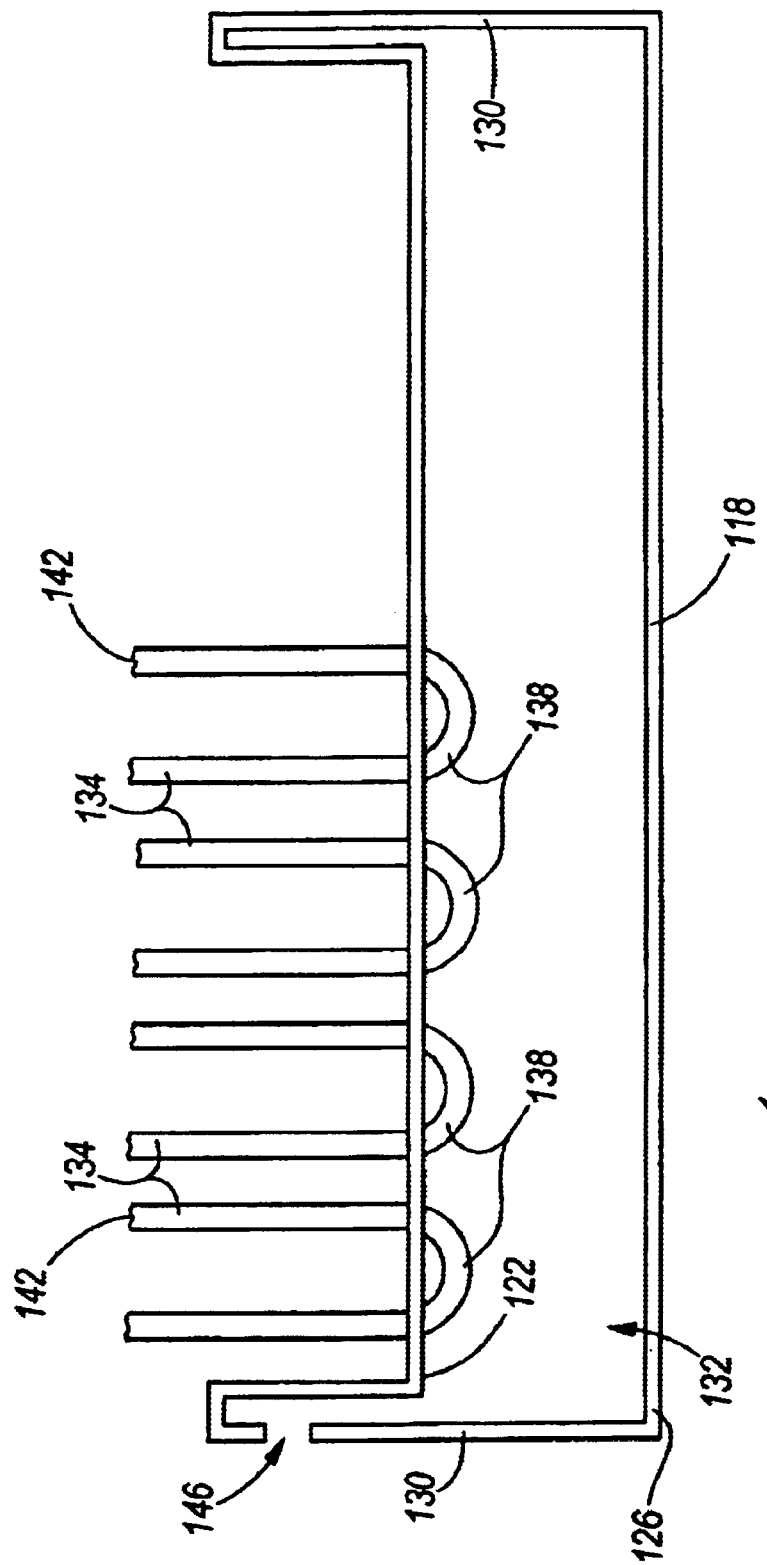
FIG. 6 is a sectional view of a fourth embodiment of the anti-microbial mat of the present invention.

FIG. 6 shows another embodiment of the present invention similar to that shown in FIG. 5. The mat 114 shown in FIG. 6 eliminates the mesh backing and the fluid-conducting layer. The mat 114 also includes a base 118 having an upper wall 122, a lower wall 126, and sidewalls 130 defining a chamber 132. Carpet fibers 134 of the mat 114 are coupled directly to the upper wall 122 such that fixed ends 138 of the fibers 134 extend below the upper wall 122 and free ends 142 of the fibers 134 extend above the upper wall 122. Similar to the mat 66 of FIG. 5, the fixed ends 138 are submerged in fluid when the chamber 132 is full such that the free ends 142 are continually moist due to capillary action within the carpet fibers 134. The mat 114 also includes an aperture 146 defined in one of the sidewalls 130, similar to the aperture 86, for introducing anti-microbial fluid into the chamber 132.

Although several specific embodiments of the invention are described above and illustrated in the figures, the invention is capable of being practiced in a variety of ways. Generally, the mat includes anti-microbial liquid that is contained within a chamber and is fluidly communicated with an absorbent upper surface. The liquid is then transferred to the soles of a persons feet, shoes, or to other objects that come into contact with the mat. The mat is reusable and refillable, either directly or by the insertion of anti-microbial containing cartridges or containers.

Each above described embodiment may also include anti-skid construction on the side walls and lower walls to prevent excessive movement of the mat on the floor as well as anti-skid construction on the carpet portions to prevent a person from slipping on the mat. The embodiments may also each be integrally constructed with other portions of flooring or carpet surfaces. Cushioning material may also be utilized in each embodiment to provide a more comfortable surface upon which a person or animal may step. Each embodiment may also include anti-fungal liquid in replacement of or in combination with the anti-bacterial liquid, as well as a moisture absorbing portion of the mat for removing excess liquid transferred to the objects which previously came into contact with the carpet fiber portions. Each embodiment may include a viewing port or other sensor device to indicate when the chamber needs to be re-filled or when a cartridge needs to be replaced. Customized graphics may be applied to the mat to improve aesthetic appearance and various fragrances may also be used in conjunction with the other microbicidal components. Additionally, various aspects of each embodiment may be combined or interchanged with aspects found in other embodiments of the invention.

Various features of the invention are set forth in the following claims.

What is claimed is:

1. A floor mat comprising:
    a base including a bottom wall and upwardly extending sidewalls defining a chamber;
    a fluid permeable upper portion at least partially supported by the sidewalls and including a fibrous upper surface that overlies the chamber;
    a removable cartridge received by the chamber and containing a cleaning liquid, the cartridge discharging the cleaning liquid to the upper portion in response to an applied pressure on the upper surface; and
    an aperture defined in at least one sidewall and sized to slidingly receive the removable cartridge.

2. The floor mat of claim 1, further comprising a fluid permeable mesh backing between the fibrous upper surface and the chamber.

3. The floor mat of claim 1, wherein the fibrous upper surface includes a plurality of carpet fibers having ends, and wherein in response to the cartridge discharging the cleaning liquid to the upper portion, the cleaning liquid is carried to the carpet fiber ends by capillary action.

4. The floor mat of claim 1, wherein the cleaning liquid includes a microbicidal component.

5. The floor mat of claim 1, wherein the cleaning liquid includes a fragrance.

6. The floor mat of claim 1, wherein the cartridge is substantially liquid impermeable until an initial applied pressure ruptures the cartridge, thereby discharging the cleaning liquid from the cartridge.

7. The floor mat of claim 1, further comprising a transparent portion defined in at least one sidewall for visual observation of an amount of the cleaning liquid in the cartridge.

8. A floor mat comprising:
a base including a bottom wall and upwardly extending sidewalls defining a chamber;
a fluid permeable upper portion at least partially supported by the sidewalls and including a fibrous upper surface that overlies the chamber; and
a removable cartridge received by the chamber and containing a cleaning liquid, the cartridge discharging the cleaning liquid to the upper portion in response to an applied pressure on the upper surface,
wherein the fibrous upper surface includes a plurality of carpet fibers having ends, and wherein in response to the cartridge discharging the cleaning liquid to the upper portion, the cleaning liquid is carried to the carpet fiber ends by capillary action.

9. The floor mat of claim 8, further comprising a fluid permeable mesh backing between the fibrous upper surface and the chamber.

10. The floor mat of claim 8, wherein the cleaning liquid includes a microbicidal component.

11. The floor mat of claim 8, wherein the cleaning liquid includes a fragrance.

12. The floor mat of claim 8, wherein the cartridge is substantially liquid impermeable until an initial applied pressure ruptures the cartridge, thereby discharging the cleaning liquid from the cartridge.

13. The floor mat of claim 8, further comprising a transparent portion defined in at least one sidewall for visual observation of an amount of the cleaning liquid in the cartridge.

14. A floor mat comprising:
a base including a bottom wall and upwardly extending sidewalls defining a chamber;
a fluid permeable upper portion at least partially supported by the sidewalls and including a fibrous upper surface that overlies the chamber; and
a removable cartridge received by the chamber and containing a cleaning liquid, the cartridge discharging the cleaning liquid to the upper portion in response to an applied pressure on the upper surface,
wherein the cartridge is substantially liquid impermeable until an initial applied pressure ruptures the cartridge, thereby discharging the cleaning liquid from the cartridge.

15. The floor mat of claim 14, further comprising a fluid permeable mesh backing between the fibrous upper surface and the chamber.

16. The floor mat of claim 14, wherein the cleaning liquid includes a microbicidal component.

17. The floor mat of claim 14, wherein the cleaning liquid includes a fragrance.

18. The floor mat of claim 14, further comprising a transparent portion defined in at least one sidewall for visual observation of an amount of the cleaning liquid in the cartridge.

19. A floor mat comprising:
a base including a bottom wall and upwardly extending sidewalls defining a chamber;
a fluid permeable upper portion at least partially supported by the sidewalls and including a fibrous upper surface that overlies the chamber;
a removable cartridge received by the chamber and containing a cleaning liquid, the cartridge discharging the cleaning liquid to the upper portion in response to an applied pressure on the upper surface; and
a transparent portion defined in at least one sidewall for visual observation of an amount of the cleaning liquid in the cartridge.

20. The floor mat of claim 19, further comprising a fluid permeable mesh backing between the fibrous upper surface and the chamber.

21. The floor mat of claim 19, wherein the cleaning liquid includes a microbicidal component.

22. The floor mat of claim 19, wherein the cleaning liquid includes a fragrance.

* * * * *